US012600819B2

(12) United States Patent
Malkoch et al.

(10) Patent No.: US 12,600,819 B2
(45) Date of Patent: Apr. 14, 2026

(54) COMPOSITION FOR FAST-CURED THERMOSETS CONTAINING AMINES, THIOLS AND UNSATURATED MOLECULES

(71) Applicant: BIOMEDICAL BONDING AB, Stockholm (SE)

(72) Inventors: Michael Malkoch, Täby (SE); Viktor Granskog, Danderyd (SE)

(73) Assignee: BIOMEDICAL BONDING AB, Stockholm (SE)

(*) Notice: Subject to any disclaimer, the term of this patent is extended or adjusted under 35 U.S.C. 154(b) by 790 days.

(21) Appl. No.: 17/783,845

(22) PCT Filed: Dec. 16, 2020

(86) PCT No.: PCT/SE2020/051218
§ 371 (c)(1),
(2) Date: Jun. 9, 2022

(87) PCT Pub. No.: WO2021/126059
PCT Pub. Date: Jun. 24, 2021

(65) Prior Publication Data

US 2023/0023748 A1 Jan. 26, 2023

(30) Foreign Application Priority Data

Dec. 17, 2019 (SE) .................................... 1951479-3

(51) Int. Cl.

| | |
|---|---|
| ***C08G 75/045*** | (2016.01) |
| ***A61K 6/62*** | (2020.01) |
| ***A61K 6/71*** | (2020.01) |
| ***A61K 6/891*** | (2020.01) |
| ***A61L 27/18*** | (2006.01) |

(52) U.S. Cl.
CPC .............. *C08G 75/045* (2013.01); *A61K 6/62* (2020.01); *A61K 6/71* (2020.01); *A61K 6/891* (2020.01); *A61L 27/18* (2013.01)

(58) Field of Classification Search
None
See application file for complete search history.

(56) References Cited

U.S. PATENT DOCUMENTS

| | | | |
|---|---|---|---|
| 2013/0123381 | A1 | 5/2013 | Bowman et al. |
| 2015/0250687 | A1 | 9/2015 | Bowman et al. |

FOREIGN PATENT DOCUMENTS

| | | | |
|---|---|---|---|
| CA | 1092135 | A | 12/1980 |
| CN | 110072564 | A | 7/2013 |
| WO | 1996/035725 | | 11/1996 |
| WO | 2016/149488 | A1 | 9/2016 |
| WO | WO2018077973 | A1 | 5/2018 |

OTHER PUBLICATIONS

Reinelt et al. Synthesis and Photopolymerization of Thiol-Modified Triazine-Based Monomers and Oligomers for the Use in Thiol-Ene-Based Dental Composites. Macromolecular chemistry and physics, Jul. 2014, vol. 215 (14), p. 1415-1425 (Year: 2015).*

CAS Database Listing for 2-dimethylaminoethyl methacrylate from ChemBook (updated Jan. 27, 2025). [online]. Retrieved form internet <URL:https://www.chemicalbook.com/ChemicalProductProperty_EN_CB2267524.htm>, [retrieved on Feb. 8, 2025] (Year: 2025).*

Arseneault, et al., "The Dawn of Thiol-Yne Triazine Triones Thermosets as a New Material Platform Suited for Hard Tissue Repair" (2018) Adv. Materials, 30:1-8.

Arseneault, et al., "The Dawn of Thiol-Yne Triazine Triones Thermosets as a New Material Platform Suited for Hard Tissue Repair" (2018) Adv. Materials, Supporting Information, pp. 1-11.

International Search Report for PCT/SE2020/051218, dated Feb. 19, 2021, 11 pages.

Podgórski, et al. "Ester free thiol-ene dental restoratives—Part A: Resin development" (2015) Dental Materials 31: 1255-1262.

Podgórski, et al. "Ester free thiol-ene dental restoratives—Part B: Composite development" (2015) Dental Materials 31: 1263-1270.

Reinelt, et al. "Synthesis and Photopolymerization of Thiol-Modified Triazine-Based Monomers and Oligomers for the Use in Thiol-Ene-Based Dental Composites" (2014) Macromol. Chem. Phys. 215:1415-1425.

Love, et al., "Amine Induced Retardation of the Radical-Mediated Thiol-Ene Reaction via the Formation of Metastable Disulfide Radical Anions", The Journal of Organic Chemistry, 2018, vol. 83; p. 2912-2919.

Office Action for Japanese patent application No. 2022537863, dated Apr. 14, 2025; 4 pages.

Khire et al., "Surface Modification Using Thiol-Acrylate Conjugate Addition Reactions", Macromolecules 2007, 40, 5669-5677.

* cited by examiner

*Primary Examiner* — Sanza L. McClendon
(74) *Attorney, Agent, or Firm* — Quarles & Brady LLP

(57) ABSTRACT

The present invention relates to a composition comprising two compounds based on triazine-trione (TATO) comprising at least one thiol group and at least one unsaturated carbon-carbon bound and where the composition further comprises an amine group or compound and a Type I photoinitiator. The composition may be used for treating teeth and bone.

22 Claims, 8 Drawing Sheets

FIG. 4A

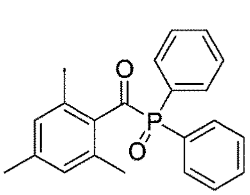

FIG. 4B

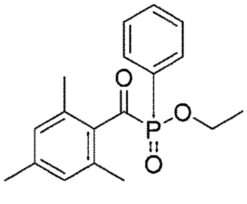

FIG. 4C

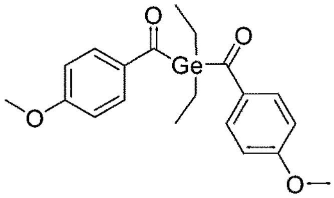

FIG. 5

| | 1st compound | 2nd compound | 3rd compound | Photo-initiator | Filler |
|---|---|---|---|---|---|
| Resin 1.0 | TEMPIC | TATATO | - | Irgacure 819* | - |
| Resin 1.1 | TEMPIC | TATATO | - | TPO | - |
| Resin 2.0 | TMTATO | TATATO | - | TPO | - |
| Resin 2.1 | TMTATO | TATATO | BADMPAPA | TPO | - |
| Resin 2.2 | TMTATO | TATATO | BADMPAPA | TPO* | HA |
| Resin 2.3 | TMTATO | TATATO | Triethylamine | TPO | - |
| Resin 2.4 | TMTATO | TATATO | | TPO-L | - |
| Resin 2.5 | TMTATO | TATATO | BADMPAPA | TPO-L | - |
| Resin 2.6 | TMTATO | TATATO | | Irgacure 819* | - |
| Resin 2.7 | TMTATO | TATATO | | Irgacure 819 | |
| Resin 2.8 | TMTATO | TATATO | BADMPAPA | Irgacure 819* | - |
| Resin 2.9 | TMTATO | TATATO | Hexamethyltriethylene-tetramine** | Irgacure 819* | - |
| Resin 2.10 | TMTATO | TATATO | | Camphorquinone | - |
| Resin 2.11 | TMTATO | TATATO | BADMPAPA | Camphorquinone | - |

* 8 μmol/g
** 19 μmol/g

| A (modified) | B (reference) | Flexural modulus of A in % of B | Flexural strength of A in % of B |
|---|---|---|---|
| Resin 2.1 | Resin 2.0 | 318 | 592 |
| Resin 2.3 | Resin 2.0 | 339 | 569 |
| Resin 2.5 | Resin 2.4 | 137 | 127 |
| Resin 2.7 | Resin 2.6 | 159 | 141 |
| Resin 2.8 | Resin 2.6 | 176 | 149 |
| Resin 2.9 | Resin 2.6 | 130 | 103 |
| Resin 2.11 | Resin 2.10 | 9 | 60 |

| | Flexural modulus (s.e.m.) [GPa] | Flexural strength (s.e.m.) [MPa] |
|---|---|---|
| Resin 1.0 | 2.5 (0.5) | 40 (4) |
| Resin 1.1 | 6.1 (0.8) | 64 (3) |
| Resin 2.0 | 2.4 (0.2) | 79 (2) |
| Resin 2.1 | 2.5 (0.1) | 98 (3) |
| Resin 2.2 | 6.3 (0.8) | 63 (10) |

| | Max load (s.e.m.) [N] |
|---|---|
| Resin 2.2 | 136 (8) |

COMPOSITION FOR FAST-CURED THERMOSETS CONTAINING AMINES, THIOLS AND UNSATURATED MOLECULES

CROSS-REFERENCE TO RELATED APPLICATION

This application claims priority to and is a 35 U.S.C. § 371 national phase application of PCT/SE2020/051218 (WO2021/126059), filed on Dec. 16, 2020, entitled "A COMPOSITION FOR FAST-CURED THERMOSETS CONTAINING AMINES, THIOLS AND UNSATURATED MOLECULES", which application claims priority to and the benefit of Sweden Patent Application No. 1951479-3, filed Dec. 17, 2019, the disclosures of which are incorporated herein by reference in their entirety.

FIELD OF THE INVENTION

The present invention relates to a composition that may be used as a light-cured resin for fracture fixation or tooth restoration. The composition provides fast curing and good mechanical properties. The present invention may be used in various applications and may be provided as a kit.

BACKGROUND

Fast-curing resin-based materials has prospered in dentistry due to their durability and their versatility of being formed into natural shapes and cured in seconds. Historically, methacrylate monomers have been used in these types of resins but with some drawbacks such as vitrification that leads to insufficient conversion of functional groups and to unreacted monomers that can leach out. Thiol-ene and thiol-yne resins polymerized via stepwise radical polymerization have been presented as alternatives to the methacrylate-based resins since their stepwise reaction leads to higher conversion of monomers. Highly crosslinked thiol-ene and thiol-yne materials have proven great potential to be used in light-cured resin-based materials such as dental or bone adhesives and composites. Generally, the thiol compounds used have been based on 3-mercaptopropionic acid or thioglycolic acid since these thiols have an ester nearby that decrease the stability of the S—H bond to easily form radicals, which lead to high reactivity in radical reactions with carbon-carbon double or triple bonds. However, these esters also make the material water sensitive by inducing water absorption and enable hydrolytic degradation, which are deteriorating properties for dental fillings or bone fixations. Also, the water absorption due to these esters can lubricate the highly crosslinked material enough to reduce its glass-transition temperature from above to below the physiological temperature of 37° C. and thus make them useless for internal structural fillings and fixations. To make more durable materials, ester-free compounds has been used. However, alkylthiols (without a nearby ester) is less reactive in radical reactions and can lower the reaction rate and lead to less crosslinked and softer materials for both radical thiol-ene and thiol-yne polymerizations since the formation of thiyl radicals are important for both initiation and propagation of the polymerization.

Catalysts or accelerators can be used to increase the reaction rate and thus enable a reduction in initiator concentration. A reduced concentration of photoinitiators improves the potential curing depth as well as decreases the amount of initiator residues that can leach out from the material and cause toxicity. Amines have frequently been used for base-catalysed thiol-ene reactions, where the reaction proceeds via Michael addition. However, when Type I radical photoinitiator version of the thiol-ene or thiol-yne reactions is used, amines are not found favourable as catalysts for fast resin reactions into hard materials. It has been disclosed that the use of amines in photoinitiated thiol-ene and thiol-yne reactions retards the reaction significantly, and has not shown any signs of benefits for fast curing of resin-based materials. Furthermore, amines have also commonly been used as co-initiators for Type II photoinitiator systems, where the amine act through electron/proton transfer with the exited Type II photoinitiator. However, in the field it is well known that in thiol-ene systems the amines are not needed since the thiols can act as co-initiators themselves. In fact, the addition of amines has shown to reduce reaction rates and final conversion in radical thiol-ene reactions. This effect has particularly been disclosed for Type I photoinitiators, where co-initiators such as amines are not participating in the photoinduced radical formation.

PCT/EP2017/077350 and PCT/EP2018/079289 discloses amine containing photoinitiated compositions of thiol-ene and thiol-yne aqueous solutions including TATATO, TMTATO, 1,3,5-tri(prop-2-yn-1-yl)-1,3,5-triazine-2,4,6-trione (TPYTATO) and 1,3,5-tri(hex-5-yn-1-yl)-1,3,5-triazine-2,4,6-trione (THYTATO), where the amine containing compound also contains phosphonic acid entities and where such compound could only be used in minimal amounts to not interfere with the adhesion properties that is highly connected to good polymerization. The presence of an amine did not show any effect since the adhesion interference was not altered if the phosphonic acid compound included an amine or not.

Fast-cured resin-based materials of thiol-ene and thiol-yne materials with high mechanical durability and low water sensitivity are needed to enable the development of the area into functional commercial products for dental and fracture restorations.

SUMMARY OF THE INVENTION

The object of the present invention is to overcome drawbacks of the prior art. The present resin compositions enable fast-cured materials without the problem of monomer leakage and with high strength in wet environments such as in bone repair and dental restoratives. The novel resins are vital for the implementation of light-cured thiol-ene or thiol-yne resins in bone and dental restorations and also distance itself from use of methacrylate resins and from use of bisphenol A derivatives which are known to be potentially harmful.

The present invention uses a photoinitiated thiol-ene or thiol-yne coupling polymerization, where the composition only reaches immediate curing upon addition of a photoinitiator and an amine catalyst. Present invention has the benefit of exploiting the high conversion of thiol-ene and thiol-yne polymerization while also being cured in seconds and can maintain as a strong material in wet conditions, features that have not earlier been presented and enable its use in clinical environments.

In a first aspect the present invention relates to a composition according to claim 1.

In a second aspect the present invention relates to a kit comprising at least two suitable containers, wherein a first container of the kit comprises a first compound having the general structure of (1)

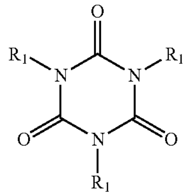

wherein R1 is a C1 to C10 alkyl group with at least one thiol group and a second container of the kit comprises a second compound having the structure of (2)

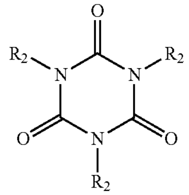

wherein R2 is a C1 to C10 alkyl group with at least one unsaturated carbon-carbon double or triple bond and wherein optionally at least one of the first or second container further comprises a third compound and wherein the first compound, the second compound and/or the optional third compound comprises at least one amine group;

wherein the optional third compound has the structure of (3)

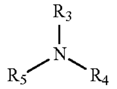

wherein at least one of R3, R4 and R5 preferably contain at least one unsaturated carbon-carbon double or triple bond or thiol;

and wherein at least one of the first, the second or an optional third container comprises a photoinitiator and optionally a stabilizer and optionally fillers.

All the embodiments described herein relates to all the aspects unless otherwise stated and all embodiment may be combined unless stated otherwise.

BRIEF DESCRIPTION OF THE FIGURES

FIG. 4A illustrates the structure of a suitable photoinitiator; Diphenyl(2,4,6-trimethylbenzoyl) phosphine oxide (TPO); FIG. 4B illustrates the structure of another suitable photoinitator; Ethyl(2,4,6-trimethylbenzoyl)phenylphosphinate; FIG. 4C illustrates the structure of another suitable photoinitator; (diethylgermanediyl)bis((4-methoxyphenyl) methanone) (Ivocerin®) U.

FIG. 5 shows a table of resin compositions.

DETAILED DESCRIPTION OF THE INVENTION

Figure 1A:
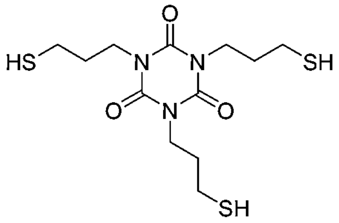
FIG. 1A illustrates the structure of a molecule suitable as the first compound in the resin composition: 1,3,5-tris(3-mercaptopropyl)-1,3,5-triazinane-2,4,6-trione (TMTATO)
Figure 1B:
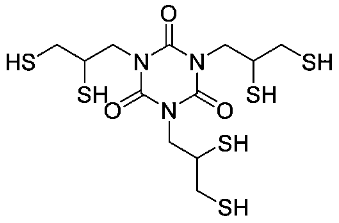
FIG. 1B illustrates the structure of another molecule suitable as the first compound in the resin composition: 1,3,5-tris(2,3-dimercaptopropyl)-1,3,5-triazinane-2,4,6-trione (TDMTATO)
Figure 1C:
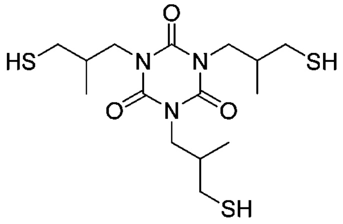
FIG. 1C illustrates the structure of another molecule suitable as the first compound in the resin composition: 1,3,5-tris(3-mercapto-2-methylpropyl)-1,3,5-triazinane-2,4,6-trione (TMMTATO).

The present inventors have shown that an amine catalyst can improve the speed of curing for thiol-ene and thiol-yne compostions via photoinitiated radicals using Type I photoinitiators. A fast curing is necessary in order to reach clinical use for these types of resin-based materials. The present invention is connected to development of a Fiber Reinforced Adhesive Patch (FRAP)—a novel concept for adhesive fixation of bone fractures that could provide a new and innovative way of treating bone fractures and defects in a range of applications. The FRAP is further described in WO2011048077 and the present invention may be used in the FRAP methodology. The present invention is also connected to thiol-ene and thiol-yne dental restoration materials and can be used together with adhesion-enhancing primers described in PCT/EP2017/077350 and PCT/EP2018/079289.

Type I photoinitiators acts through a cleavaging reaction into two radical fragments of the original photoinitiator. The irradiation with UV-light leads to a homolytic bondage cleavage and generation of two highly reactive radical species. These radicals then initiate the polymerization.

Until now, problems with curing and durability of resin-based materials of thiol-ene and thiol-yne have hindered the expansion of these materials for use in clinical situations for bone and tooth repair. However, the present inventors have developed a new fast-curing photoinitiated resin composition that can solve these critical problems. The resin-based material has several applications areas such as in tooth filling and dental restorations and will as well enable the emerging technology transfer of resin-based materials into bone fracture surgery, such as FRAP, where current methacrylate based dental materials are not suitable from a toxicology point of view.

The concept is based on years of research into the materials utilization and performance. Mechanical tests direct after curing and 24 hours after curing display the significant improvement of the curing of the present invention in comparison to a general composition described in literature. The composition has proven useful in ex vivo fixation of bone fractures and in animal trials on rat femur fractures. The composition has also been used for initial ex vivo teeth restorations with promising results.

An advantage of the present composition is that it cures fast, exhibits negligible leakage of monomers, provides higher strength and higher reproducibility (low standard deviation).

The Composition

The composition according to the present invention comprises a first compound, a second compound and optionally a third compound. The first compound has the general structure of a (1)

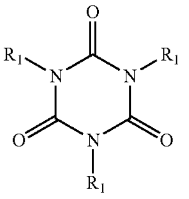

wherein R1 is a C1 to C10 alkyl group with at least one thiol group and a second compound having the structure of (2)

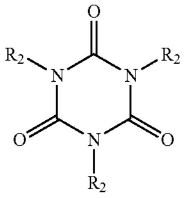

wherein R2 is a C1 to C10 alkyl group with at least one unsaturated carbon-carbon double or triple bond and optionally a third compound. At least one of the first compound, the second compound or the optional third compound comprises at least one amine group. The structure of the first and the second compound may be described to be based on triazine-trione (TATO). The composition further comprises a Type I photoinitiator preferably selected from a peroxide, nitrile, phosphine oxide and germanium based photoinitiator, and optionally a stabilizer. In a preferred embodiment the composition is contained in a light protected or shielded container in order to avoid premature activation of the photoinitiator.

Furthermore, in one embodiment one of the first compound, the second compound and the optional third compound comprises at least one amine group. In one embodiment preferably the third compound comprises at least one amine group, and more preferably the third compound comprises at least one amine group and at least one carbon-carbon double or triple bond or thiol. The composition further comprises a photoinitiator and optionally a stabilizer.

The addition of amine containing molecules to the thiol-ene or thiol-yne composition containing the first compound and the second compound was found to be a major factor in order to increase the curing speed of the composition from hours to seconds using photoinitiated polymerization. The increase in curing speed was surprising since the current view of amines in radical thiol-ene and thiol-yne reactions is that it retards the reaction rate. Another surprising effect is that the amine groups does not act as an initiator to any major extent and thereby no significant prepolymerization via Michael-addition reaction occurs leading to a premature curing and an unusable mixture. Thus, an unpredictably fast-curing but yet stable composition is presented herein that can be used for several hours after mixing as a photoinitiated resin without inducing significant prepolymerization, which enables its use in a clinical setting.

The first compound may be any suitable thiol compound according to structure (1). The first compound may comprise one, two or three thiol groups. In one embodiment the first compound comprises at least two or preferably at least three thiol groups. In one preferred embodiment the first compound is selected from TMTATO, 1,3,5-tris(2,3-dimercaptopropyl)-1,3,5-triazinane-2,4,6-trione (TDMTATO) or 1,3,5-tris(3-mercapto-2-methylpropyl)-1,3,5-triazinane-2,4,6-trione (TMMTATO). In another embodiment the first compound is preferably TMTATO. In one embodiment the amount of the first compound is 20 to 90 wt % of the total amount of the first, the second and the optional third compound, preferably 30 to 80 wt %, or more preferably 40 to 60 wt %. Without being bound by theory but these amounts are believed to result in thermosets with improved properties.

Figure 2A:
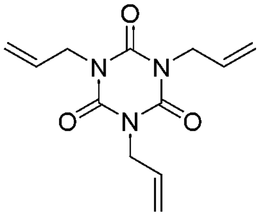
FIG. 2A illustrates the structure of a molecule suitable as the second compound in the resin composition: 1,3,5-triallyl-1,3,5-triazinane-2,4,6-trione (TATATO)
Figure 2B:
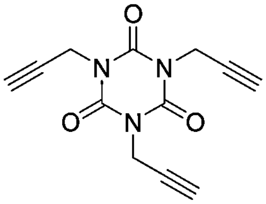
FIG. 2B illustrates the structure of another molecule suitable as the second compound in the resin composition: 1,3,5-tri (prop-2-yn-1-yl)-1,3,5-triazinane-2,4,6-trione (TPYTATO)
Figure 2C:
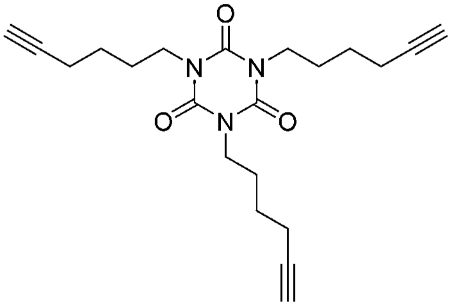
FIG. 2C illustrates the structure of another molecule suitable as the second compound in the resin composition: 1,3,5-tri (hex-5-yn-1-yl)-1,3,5-triazinane-2,4,6-trione (THYTATO).
Figure 3A:
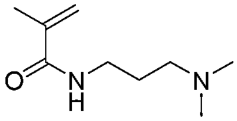
FIG. 3A illustrates the structure of a molecule suitable as the third compound in the resin: N-(3-(dimethylamino) propyl) methacrylamide (DMAPMA)
Figure 3B:
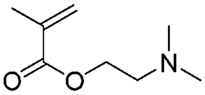
FIG. 3B illustrates the structure of another molecule suitable as the third compound in the resin: 2-(dimethylamino)ethyl methacrylate (DMAEMA)
Figure 3C:
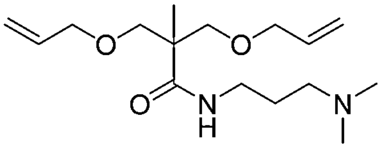
FIG. 3C illustrates the structure of another molecule suitable as the third compound in the resin: 3-(allyloxy)-2-((allyloxy)methyl)-N-(3-(dimethylamino) propyl)-2-methylpropanamide (BADMPAPA)
Figure 3D:
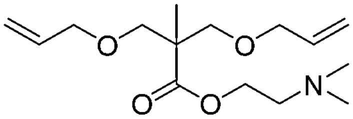
FIG. 3D illustrates the structure of another molecule suitable as the third compound in the resin: 2-(dimethylamino)ethyl 3-(allyloxy)-2-((allyloxy)methyl)-2-methylpropanoate (BAD-MEAPA)
Figure 3E:
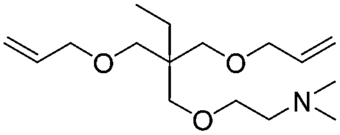
FIG. 3E illustrates the structure of another molecule suitable as the third compound in the resin: 2-(2,2-bis ((allyloxy) methyl) butoxy)-N,N-dimethylethan-1-amine.
Figure 3F:
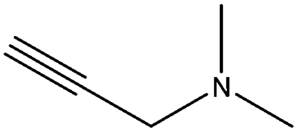
FIG. 3F illustrates the structure of another molecule suitable as the third compound in the resin: 3-dimethylamino-1-propyne.
Figure 3G:
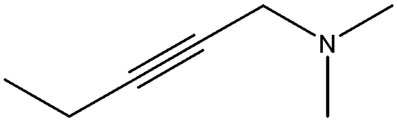
FIG. 3G illustrates the structure of another molecule suitable as the third compound in the resin: 1-dimethylamino-2-pentyne.
Figure 3H:
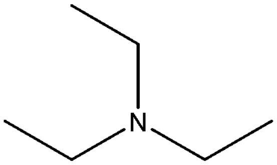
FIG. 3H illustrates the structure of another molecule suitable as the third compound in the resin: triethylamine.
Figure 3I:
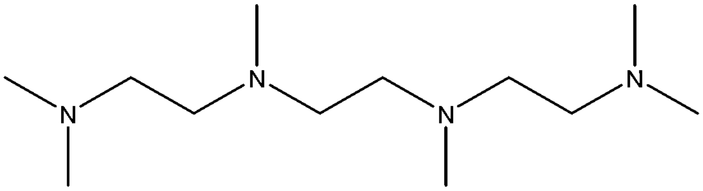
FIG. 3I illustrates the structure of another molecule suitable as the third compound in the resin: 1,1,4,7,10,10-Hexamethyltriethylenetetramine.

The second compound may be any suitable unsaturated compound. The second compound may comprise at least three unsaturated carbon-carbon double or triple bonds. In one embodiment the second compound comprises an allyl group or a terminal or non-terminal double bond or a terminal or a non-terminal triple bond. In FIG. 2 non-limiting examples of suitable second compounds are disclosed. In one embodiment the second compound is selected from 1,3,5-triallyl-1,3,5-triazinane-2,4,6-trione (TATATO), 1,3,5-tri(prop-2-yn-1-yl)-1,3,5-triazinane-2,4,6-trione (TPYTATO) or 1,3,5-tri(hex-5-yn-1-yl)-1,3,5-triazinane-2,4,6-trione (THYTATO). In another embodiment the second compound is TATATO. In one embodiment the amount of the second compound is 10 to 80 wt % of the total amount of the first, the second and the optional third compound, preferably 10 to 60 wt %, or more preferably 10 to 50 wt %.

In yet another embodiment the amount of the first compound is 20 to 90 wt % of the total amount of the first, the second and the optional third compound, preferably 30 to 80 wt %, or more preferably 40 to 60 wt % and the amount of the second compound is 10 to 80 wt % of the total amount of the first, the second and the optional third compound, preferably 10 to 60 wt %, or more preferably 10 to 50 wt %.

The optional third compound may be any suitable amine containing compound. In one embodiment the optional third compound has the general structure of

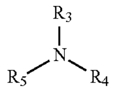

(3)

wherein at least one of R3, R4 and R5 preferably contain at least one unsaturated carbon-carbon double or triple bond or thiol. Each R3, R4 and R5 may be any suitable substituent preferably hydrogen or an alkyl, alkylene, alkoxy, alkyl ester, alkyl ether, methacrylic group, alkyl amide, methacrylamide or the corresponding conjugated acid. In a preferred embodiment R3 is a group containing at least one unsaturated carbon-carbon double, triple bond or thiol such as a double bond containing group such as a vinyl group, acrylate, methacrylate group or an methacrylamide group or a triple bond or a thiol and R4 and R5 may be any suitable substituent preferably hydrogen or an alkyl, alkylene, alkoxy, alkyl ester, alkyl ether, methacrylic group, alkyl amide, methacrylamide. In a preferred embodiment the R3, R4 and R5 groups are selected so that the pKa of the third compound, or its conjugated acid, is higher than 3, preferably higher than 6, more preferably higher than 10 and more preferably between 8 and 13. In another embodiment none of R3, R4 and R5 is a trivalent phosphorous containing group such as phosphonic acid group. Such groups make the compound acidic which is believed to be disadvantage in certain applications. The third compound acts as a catalyst and an advantage of using a catalyst comprising double, triple bonds or thiol is that they may be incorporated into the formed polymer or thermoset and thereby reducing the potential leakage of the catalyst. In one embodiment the optional third compound is selected from N-(3-(dimethylamino)propyl)methacrylamide (DMAPMA), 2-(dimethylamino)ethyl methacrylate (DMAEMA), 3-(allyloxy)-2-((allyloxy)methyl)-N-(3-(dimethylamino)propyl)-2-methylpropanamide (BADMPAPA), 2-(dimethylamino)ethyl 3-(allyloxy)-2-((allyloxy)methyl)-2-methylpropanoate (BADMEAPA), 2-(2,2-bis((allyloxy)methyl)butoxy)-N,N-dimethylethan-1-amine, 3-dimethylamino-1-propyne, 1-dimethylamino-2-pentyne, triethylamine and 1,1,4,7,10,10-Hexamethyltriethylenetetramine. In another embodiment the third compound is DMAPMA. In another embodiment third compound is BADMPAPA. In one embodiment the amount of the optionally third compound is 0.1 to 50 wt % of the total amount of the first, the second and the optional third compound, preferably 0.5 to 30 wt %, or more preferably 1 to 10 wt %.

In one embodiment the molar amount of amine groups to thiol groups in the composition is between 0.1 to 200 mol % such as 0.1 to 50 mol % or 0.1 to 20 mol % or 0.1 to 5 mol %.

In yet another embodiment the amount of the first compound is 20 to 90 wt % of the total amount of the first, the second and the optional third compound, preferably 30 to 80 wt %, or more preferably 40 to 60 wt % and the amount of the second compound is 10 to 80 wt % of the total amount of the first, the second and the optional third compound, preferably 10 to 60 wt %, or more preferably 10 to 50 wt % and wherein the molar amount of amine groups to thiol groups in the composition is between 0.1 to 200 mol % such as 0.1 to 50 mol % or 0.1 to 20 mol % or 0.1 to 5 mol %.

In one embodiment the ratio of functionality between thiol groups and unsaturated groups such as double or triple bonds in the composition is between 1.10:1 to 1:1.10 or more preferably between 1.05:1 to 1:1.05 or more preferably between 1.01:1 to 1:1.01, where a thiol group counts as a functionality of one, a double bond counts as a functionality of one and a triple bond counts as a functionality of two.

In yet another embodiment the amount of the first compound is 20 to 90 wt % of the total amount of the first, the second and the optional third compound, preferably 30 to 80 wt %, or more preferably 40 to 60 wt % and the amount of the second compound is 10 to 80 wt % of the total amount of the first, the second and the optional third compound, preferably 10 to 60 wt %, or more preferably 10 to 50 wt % and wherein the ratio of functionality between thiol groups and unsaturated groups such as double or triple bonds in the composition is between 1.10:1 to 1:1.10 or more preferably between 1.05:1 to 1:1.05 or more preferably between 1.01:1 to 1:1.01.

Any suitable Type 1 photoinitiator may be used. The initiator is preferably a peroxide, nitrile, phosphine oxide or germanium based susceptible to radiation to create reactive species. In one embodiment the photo initiator is selected from diphenyl(2,4,6-trimethylbenzoyl)phosphine oxide (TPO), ethyl(2,4,6,-trimethylbenzoyl)phenylphosphinate (TPO-L), bis(4-methoxybenzoyl)diethyl-germanium (Ivocerin). The amount of photo initiator may be 0.05 to 5 wt % of the total amount of the composition such as 0.1 to 2 wt %.

In yet another embodiment the amount of the first compound is 20 to 90 wt % of the total amount of the first, the second and the optional third compound, preferably 30 to 80 wt %, or more preferably 40 to 60 wt % and the amount of the second compound is 10 to 80 wt % of the total amount of the first, the second and the optional third compound, preferably 10 to 60 wt %, or more preferably 10 to 50 wt % and wherein the amount of photo initiator may be 0.05 to 5 wt % of the total amount of the composition such as 0.1 to 2 wt %.

Any suitable stabilizer may be used. The stabilizer is preferably selected from but not limited to phenolics, quinones or phosphorous compounds. In one embodiment the stabilizer is catechol or catechol derivatives. In one embodiment the amount of stabilizer is 0.05 to 5 wt % of the total amount of the composition preferably 0.5 to 3 wt %.

In order to improve the rheological properties of the resin composition and mechanical properties of the cured material, especially when used in bone fixation or tooth restoration, fillers can be added to the resin mixtures. The fillers may be any suitable filler. The fillers may contain but are not limited to ceramics such as metal salts of phosphate, sulfate, oxide form or polymers or metals. In a preferred embodiment the additive is glass or hydroxyapatite particles or preferably hydroxyapatite particles. The fillers may be but are not limited to the form of crystals, spheres, rods, flakes, fibers or non-uniform particles. In one embodiment the fillers are functionalized to contain one or more carbon-carbon double or triple bond and/or one or more thiol group.

The composition may comprise any suitable solvent but preferably the composition is essentially free or completely free of any solvent. In one embodiment the composition comprises less than 5 wt % of solvent, preferably less than 1 wt %. In one embodiment the composition comprises water, preferably less than 5 wt %, more preferably less than 1 wt %.

Applications

The present invention may be used as a resin-based material for example when treating hard tissue such as bone and tooth. The composition can be used in combination with a primer or an adhesive or a fiber sheet or a screw or a plate for the fixation of bone fractures or for tooth restoration. The composition can be applied at site and formed to wanted shape and then cured into a hard and strong material using a light-source.

Kit

The present invention further relates to a kit in order to provide and apply the resin composition. The kit contains at least two suitable containers, a first and a second container, and optionally a third container wherein the first one container comprises a first compound having the general structure of a (triazine-trione (TATO))

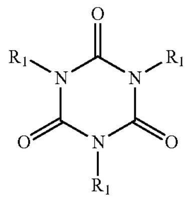

(1)

wherein R1 is a C1 to C10 alkyl group with at least one thiol group. The second container comprises a second compound having the structure of

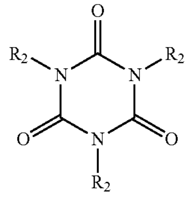

(2)

wherein R2 is a C1 to C10 alkyl group with at least one unsaturated carbon-carbon double or triple bond. At least one of the first, second or optional third container may further comprise an optional third compound and at least one of the first compound, the second compound and/or the optional third compound comprises at least one amine group. The optional third compound has the structure of

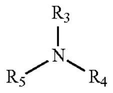

(3)

wherein at least one of R3, R4 and R5 preferably contain at least one unsaturated carbon-carbon double or triple bond or thiol;

At least one of the containers includes a photoinitiator and optionally at least one of the containers of the kit comprises a stabilizer and optionally fillers. In one embodiment the first container further comprises the optional third compound. In another embodiment the second container further comprises the optional third compound. In one embodiment the filler is in third container wherein the third container preferably do not comprise the first compound, the second compound and the optional third compound.

EXAMPLES

Example 1

FIG. 5 display examples of compounds in resin mixtures using equimolar amounts of thiol and unsaturated functionalities, 75 μmol/g amine and 16 μmol/g of initiator and a filler content of 56 wt % if not stated otherwise. The components were added to a vial and mixed together with a spatula at room temperature and normal air conditions. The initiator was added in dark conditions and the vial was at all times protected from light with aluminum foil.

Example 2

Figure 6A:
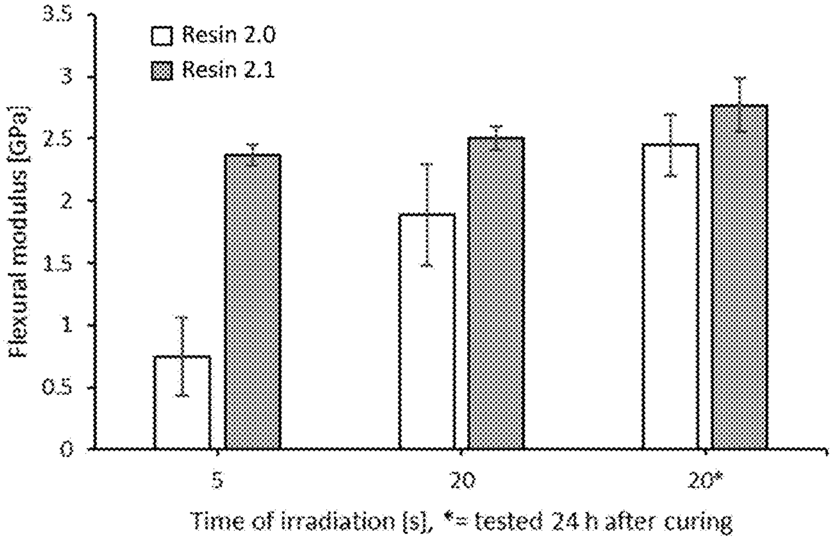
FIG. 6A shows mechanical properties of a flexural modulus.
Figure 6B:
FIG. 6B shows flexural strength of resins where varying irradiation and curing times was used.
Figures 6C, 6D:
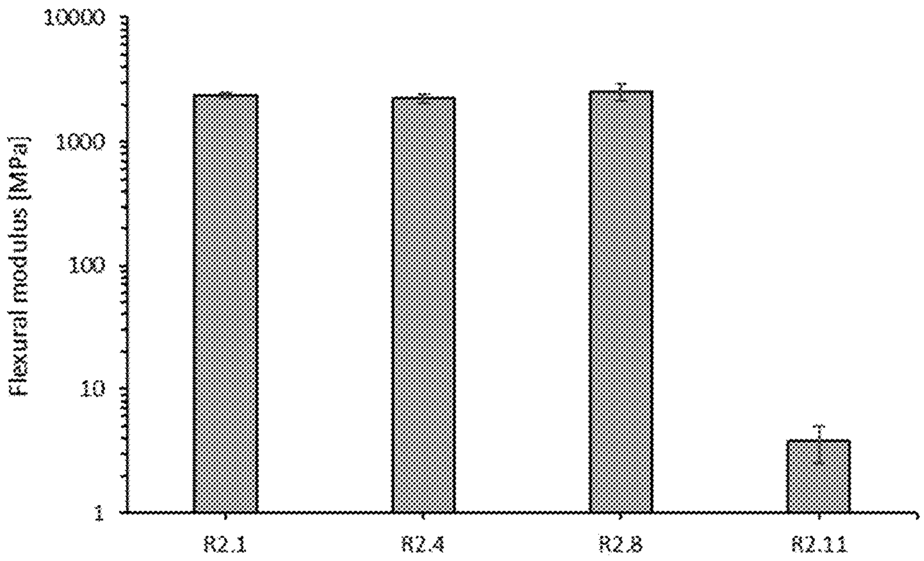
FIG. 6C shows flexural modulus of resins after 5 seconds of irradiation.
FIG. 6D shows flexural modulus and strength after 5 seconds of irradiation of modified resins relative to its reference, values in %.

Flexural bending test: 35×5×1 mm rectangular beams were prepared by spreading different resin compositions according to the present invention into silicone molds and cured with a Bluephase 20i (Ivoclar Vivadent) lamp for 5, 10 or 20 seconds per unit area using light with a wavelength of 385-500 nm and a light intensity of 2000 mW/cm2. The beams mounted on a three-point bending set-up on a universal tensile testing machine immediately or 24 h after curing. A support span of 30 mm and cross-head speed of 5 mm/min were used. Results in FIG. 6.

Key conclusions: The addition of an amine-catalyst enable an instant high-performance material upon polymerization, while longer curing times are necessary without an amine-catalyst. The tests with Type I photoinitiators showed an improvement of the mechanical durability with addition of an amine as catalyst. The addition of an amine combined with Irgacure 819 provided an equal improvement as doubling the amount of initiator. Tests with Type II initiator camphorquinone display said initiator's inability to perform well in the conditions used, despite optimal light-wavelengths, and is not a suitable initiator for these types of materials. Also, the amount of amine used in this test lowered the mechanical performance significantly together with camphorquinone.

Example 3

Figure 7:
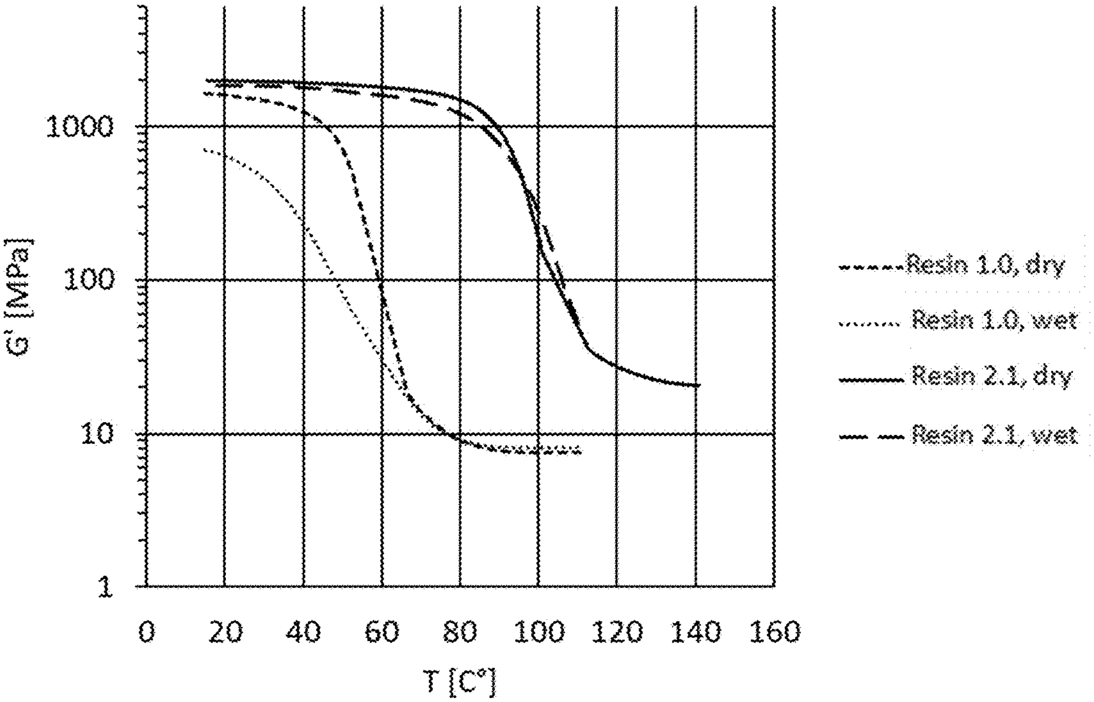
FIG. 7 shows the effect of water absorption on the storage modulus with an increased temperature from dynamic mechanical analysis.

Glass transition analysis: Dynamic mechanical analysis were performed on different resin compositions according to the present invention on a TA Instruments (New Castle, DE, USA) DMA Q800 in tensile mode, with a material geometry of (1.5×6.5×2.5 mm). A temperature ramp from 20° C. up to 110° C. or 140° C., depending on material requirements to reach the rubber plateau, with a heating rate of 10° C./min. A strain of 0.1% was induced with a frequency of 1 Hz. Results in FIG. 7.

Key conclusion: The ester-free TATO material including an amine-catalyst shows a high glass-transition temperature ($T_g$) that remained well above 50° C. and the mechanical properties will not be significantly different in physiological environment compared to the laboratory environment of conducted tests. The ester-based TATO material shows an onset $T_g$ around 30° C. upon water absorption and will become softer in an physiological environment compared to the laboratory environment of conducted tests.

Example 4

Figure 8A:
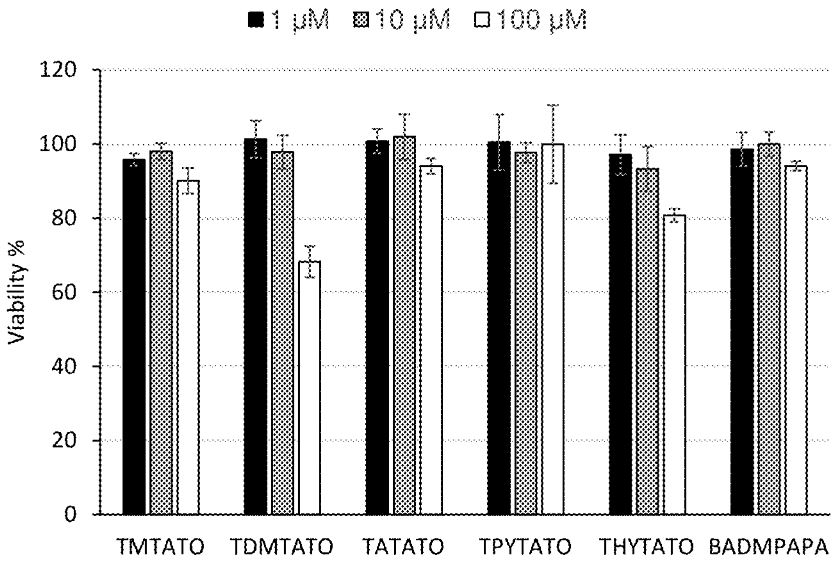
FIG. 8A shows cytotoxicity of suitable monomers.
Figure 8B:
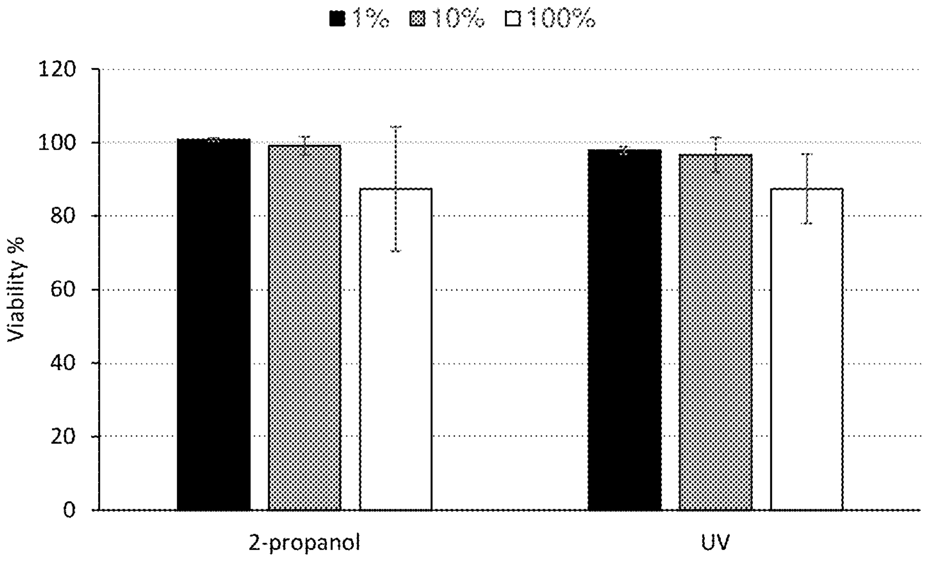
FIG. 8B shows cured resin 2.2 sterilized with either 2-propanol or UV-light.

Cytotoxicity of compounds was evaluated through in vitro cell viability tests. RAW 264.7 cells were maintained in DMEM medium with 10% FBS and 100 U penicillin-streptomycin solution. Cells were washed and harvest through trypsin and transferred into 96 well plates a density of 5000 cells/well and incubated for 24 h before use. The components were dissolved in DMSO and diluted in DMEM to prepare working medium with final concentrations 1, 10, 100 μM of the components. Old DMEM was removed from cells and replaced by fresh working medium above and incubated for another 24 h. Then AlamarBlue tests were performed according to the general instructions. Data were acquired with plate reader Infinite® M200 (Tecan, Switzerland)) with fluorescent model ex/em wavelength at 560/590 nm. Data were acquired using i-control™ software. In all cases, 6 replicate wells were set for each sample and cells treated with PBS were used as negative control. Each test was repeated three times. Also, an elution test was performed to evaluate in vitro toxicity of the crosslinked material 2.2. The material was sterilized with 2-propanol or with UV-light for 3 h. The samples were then incubated in complete DMEM medium in a concentration of 10 mg/ml for 24 h to allow potential compounds leach out. Then the testing medium were transferred into 96-well plate (Raw 264.7 5000 cells/well) with 100 ul/well and incubated with another 72 h. MTT test was applied for the viability evaluation and data were acquired with plate reader Infinite® M200 (Tecan, Switzerland)) at 570 nm. For each sample, 3 parallel pieces were prepared to obtain leached-out medium for each cell line. For each piece of material, 6 parallel wells were conducted in MTT assay. Results in FIG. 8.

Key conclusions: RAW 264.7 cells show high tolerance to the tested compounds and the crosslinked material 2.2 did not leach compounds to cause a toxic effect on Raw 264.7 cells.

Example 5

Figures 9, 10, 11:
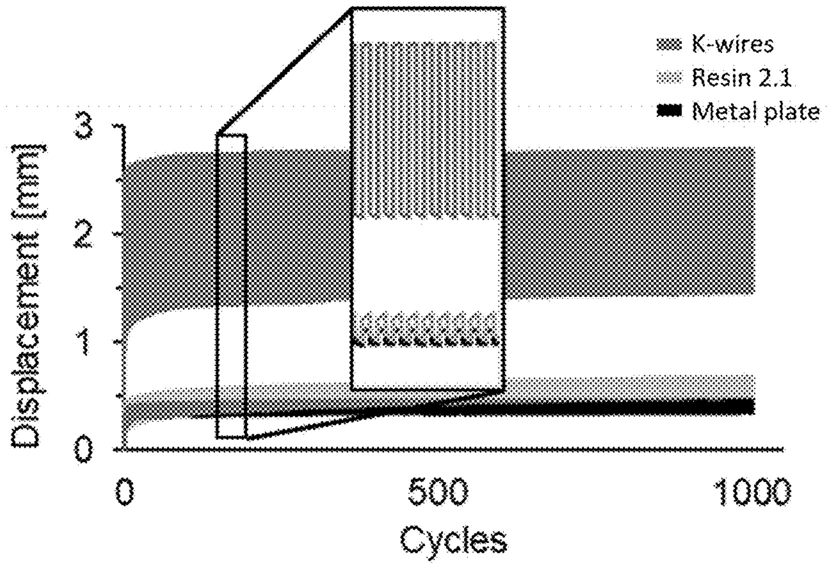
FIG. 9 shows the flexural modulus and strength of different cured resins from three-point bending tests.
FIG. 10 shows the maximum load of bone fracture fixation model.
FIG. 11 shows the representation of cyclic load data of bone fracture fixation model.

Flexural bending test: 35×5×1 mm rectangular beams were prepared by spreading resin compositions according to the present invention into silicone molds and cured with a Bluephase 20i (Ivoclar Vivadent) lamp for 20 seconds per unit area using light with a wavelength of 385-500 nm and a light intensity of 2000 mW/cm$^2$. The beams mounted on a three-point bending set-up on a universal tensile testing machine 24 h after curing. A support span of 30 mm and cross-head speed of 5 mm/min were used. Results in FIG. 9.

Key conclusions: Rigid and strong materials can be made from tested resins.

Example 6

The second and fifth metacarpal was dissected from porcine feet obtained from a butcher shop. The metacarpals were cleaned from soft tissue and a transverse fracture was cut through the bone pieces. Two screws were placed on each side of the bone fracture. The screws were screwed half-way in, and resin 2.2 was applied around them and across the fracture. Then, the screws were fully screwed in and the adhesive was cured using a light emitting diode (LED) polymerization lamp (Bluephase® 20i), with wavelengths of 385-515 nm with a dominant wavelength of 470 and 400 nm and an intensity of 2000-2200 mW/cm2, intended for light-cured dental materials. The total time of irradiation was 10 s per cm$^2$. Then the screws were, covered with Resin 2.2 and a fiber mesh followed by curing with light irradiation. Finally, a thin layer of adhesive was applied followed by curing. Three-point bending tests were made using an Instron 5566 instrument, Instron Korea LLC. The load was measured with a 10 kN load cell and a continuous displacement of 5 mm/min was used. A pre-load of 1 N and a span length between the lower supports of 3 cm was used. For the fatigue tests a 500 N load cell was used and a cyclic force from 10 N to 70 N was applied with a cross-head speed of 25 mm/min. A pre-load of 10 N and a pre-load speed of 5 mm/min were used. Kirschner wire and LCP Compact Hand Locking strut plate 1.5 were used as reference fixators. The measurements were conducted at 23° C. and a relative humidity of 50%. The specimens were kept wet as long as possible until they were placed in the machine. Data were collected using the Bluehill software. Results in FIGS. 10 and 11.

Key conclusions: Resin 2.2 show a high strength when used as fixator in a finger fracture model.

The invention claimed is:

1. A composition comprising a first compound, a second compound and a third compound; wherein the first compound has the general structure according to (1)

(1)

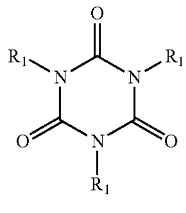

wherein each R1 is individually a C1 to C10 alkyl group and wherein at least one of the R1 comprises at least one thiol group; wherein the second compound has the general structure according to (2)

(2)

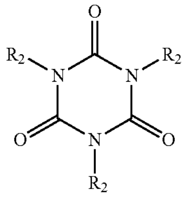

wherein each R2 is individually a C1 to C10 alkyl group and wherein at least one of the R2 comprises at least one unsaturated carbon-carbon double or triple bond;

wherein the third compound is an amine containing compound; and wherein the composition further comprises a Type I photoinitiator and optionally a stabilizer;

wherein the molar amount of amine groups to thiol groups in the composition is between 0.1 to 100 mol %; and wherein the amount of the third compound is 0.1 to 50 wt % of all the total amount of the first, second and third compound.

2. The composition according to claim 1 wherein the third compound have at least one carbon-carbon double bond, at least one carbon-carbon triple bond or at least one thiol.

3. The composition according to claim 1 wherein the first compound is selected from TMTATO, 1,3,5-tris(2,3-dimercaptopropyl)-1,3,5-triazinane-2,4,6-trione (TDMTATO) or 1,3,5-tris(3-mercapto-2-methylpropyl)-1,3,5-triazinane-2,4,6-trione (TMMTATO).

4. The composition according to claim 1 wherein the second compound is 1,3,5-triallyl-1,3,5-triazinane-2,4,6-trione (TATATO), 1,3,5-tri (prop-2-yn-1-yl)-1,3,5-triazinane-2,4,6-trione (TPYTATO) or 1,3,5-tri (hex-5-yn-1-yl)-1,3,5-triazinane-2,4,6-trione (THYTATO).

5. The composition according to claim 1 wherein the composition comprises a third compound having the structure of (3)

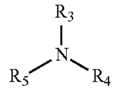

wherein at least one of R3, R4 and R5 contain at least one unsaturated carbon-carbon double or triple bond or thiol.

6. The composition according to claim 1 wherein the composition comprises a third compound selected from N-(3-(dimethylamino) propyl) methacrylamide (DMAPMA) or 3-(allyloxy)-2-((allyloxy)methyl)-N-(3-(dimethylamino) propyl)-2-methylpropanamide (BADMAPA).

7. The composition according to claim 1 wherein the amount of the first compound is 20 to 90 wt % of all the total amount of the first, second and third compound.

8. The composition according to claim 1 wherein the amount of the second compound is 10 to 80 wt % of all the total amount of the first, second and third compound.

9. The composition according to claim 1 wherein the optional third compound has a pKa of more than 3.

10. The composition according to claim 1 wherein the composition comprises a stabilizer and wherein the stabilizer is a phenolic, quinone or phosphorous compound.

11. The composition according to claim 1 wherein the amount of stabilizer is 0.05 to 5 wt %.

12. The composition according to claim 1 wherein the composition contains fillers.

13. The composition according to claim 1 wherein the amount of fillers are 20 to 90 wt %.

14. The composition according to claim 1 wherein the composition is essentially free or completely free of any solvent.

15. The composition according to claim 1 wherein the ratio of functionality between thiol groups and unsaturated groups such as double or triple bonds in the composition is between 1.10:1 to 1:1.10.

16. The composition according to claim 1 wherein the molar amount of amine groups to thiol groups in the composition is between 0.1 to 20 mol.

17. The composition according to claim 1 wherein the optional-third compound does not contain a trivalent phosphorous containing group such as a phosphonic acid group.

18. The composition according to claim 1 wherein the Type I photoinitiator is selected from a peroxide, a nitrile, a phosphine oxide or a germanium based photoinitiator.

19. A kit comprising at least two suitable containers, whereas a first container of the kit comprises a first compound having the general structure of (1)

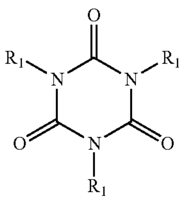

wherein R1 is a C1 to C10 alkyl group with at least one thiol group and a second container of the kit comprises a second compound having the structure of (2)

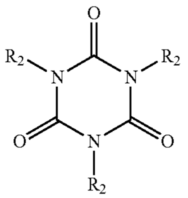

wherein R2 is a C to C10 alkyl group with at least one unsaturated carbon-carbon double or triple bond and wherein at least one of the first, second or an optional third container further comprises a third compound;

wherein the third compound is an amine containing compound;

and wherein at least one of the first, the second or optional third container comprises a Type I photoinitiator and optionally a stabilizer and optionally fillers;

wherein the molar amount of amine groups to thiol groups in the composition is between 0.1 to 100 mol %; and wherein the amount of the third compound is 0.1 to 50 wt % of all the total amount of the first, second and third compound.

20. The composition according to claim 1 wherein the optional-third compound has a pKa in between 8 and 13.

21. The composition according to claim 1 wherein the ratio of functionality between thiol groups and unsaturated groups such as double or triple bonds in the composition is between 1.05:1 to 1:1.05.

22. The composition according to claim 1 wherein the molar amount of amine groups to thiol groups in the composition is between 0.1 to 5 mol %.

* * * * *